United States Patent [19]

Butas

[11] Patent Number: 4,906,936
[45] Date of Patent: Mar. 6, 1990

[54] ELECTRIC CONDUCTIVITY SENSOR FOR MEASURING THE LENGTH AND NUMBER OF FIBERS IN AN AQUEOUS SUSPENSION

[75] Inventor: Rudolf Butaš, Moravsk J',acu/a/ n, Czechoslovakia

[73] Assignee: Vyskumny ustav papieru a celulozy, Bratislava, Czechoslovakia

[21] Appl. No.: 210,680

[22] Filed: Jun. 17, 1988

[30] Foreign Application Priority Data

Jun. 18, 1988 [CS] Czechoslovakia .................... 4493-87

[51] Int. Cl.$^4$ ...................... G01N 15/02; G01N 27/00
[52] U.S. Cl. .................................... 324/446; 324/449; 324/71.4
[58] Field of Search ...................... 324/446, 439, 71.4, 324/449; 73/863.41, 864.81; 137/551, 559

[56] References Cited

U.S. PATENT DOCUMENTS

| | | | |
|---|---|---|---|
| 3,390,326 | 6/1968 | Imadate | 324/71.4 |
| 3,472,371 | 10/1969 | Ayerst | 324/71.4 |
| 4,220,499 | 9/1980 | Hughes | 324/71.4 |
| 4,284,496 | 8/1981 | Newton | 324/71.4 |
| 4,390,842 | 6/1983 | Wygant | 324/71.4 |

FOREIGN PATENT DOCUMENTS

| | | | |
|---|---|---|---|
| 527640 | 8/1977 | U.S.S.R. | |
| 1203424 | 1/1986 | U.S.S.R. | 324/439 |

Primary Examiner—Reinhard J. Eisenzopf
Assistant Examiner—Jose M. Solis
Attorney, Agent, or Firm—Klein & Vibber

[57] ABSTRACT

Device for measuring the length and number of fibers in an aqueous suspension has a sensor with an upper and lower electrode with an insulating part between the electrodes, a rectifying channel having an inlet and outlet part, the first in close contact with the upper electrode, the second in close contact with the lower electrode, with mutually aligned openings of the sensor and the rectifying means. This arrangement can be applied for such suspensions of fibers or other particles, the electric conductivity of which is different from the conductivity of their carrying medium.

7 Claims, 1 Drawing Sheet

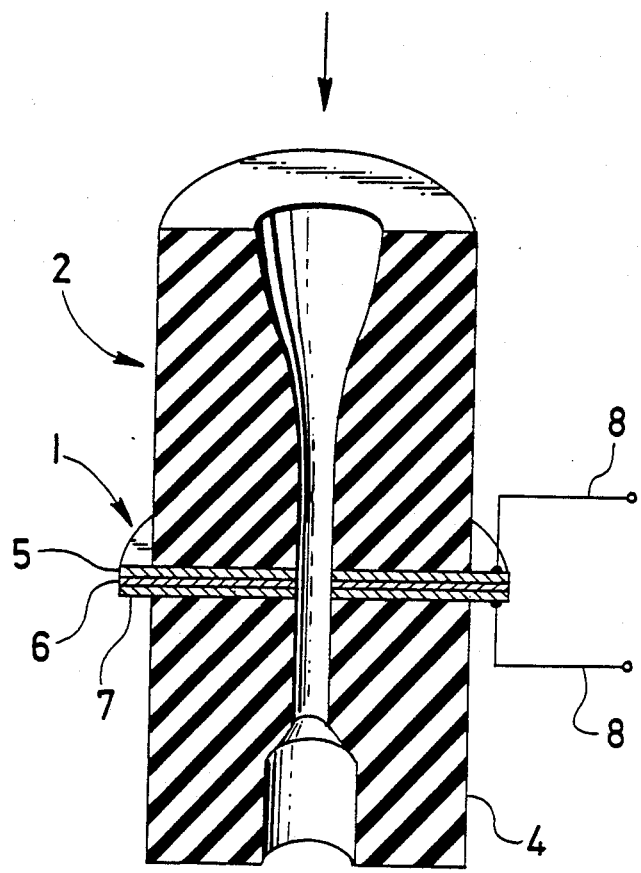

ELECTRIC CONDUCTIVITY SENSOR FOR MEASURING THE LENGTH AND NUMBER OF FIBERS IN AN AQUEOUS SUSPENSION

FIELD OF THE INVENTION

The invention relates to a sensor of electric conductivity for measuring the length and number of fibers in an aqueous suspension, where the design of the sensor and its interconnection in a circuit of a through flowing carrying medium is disclosed. The invention is useful in the paper and pulp industry where the length and number of fibers in an aqueous suspension is necessary to determine pulp quality.

BACKGROUND OF THE INVENTION

Known sensors of electric conductivity for said kind of application are, for example the apparatus known as "ADSV" from the USSR Inventor's Certificate No. 527,640. These known sensors, however, have the drawback that their design cannot provide an arrangement capable of orienting the fibers as to their length with respect to the inlet opening of the sensor means. The speed of the suspension in the opening of the sensor means is substantially higher than in the close neighbourhood of the sensor means, causing differences of speed of the carrying medium of the suspension and of the fibers. The sensor means of the mentioned apparatus "ADSV" is submersible and does not enable a sucking off of the measured suspension without a residuum, which represents a drawback where a defined weight of fibers in a suspension has to be measured.

Another known device is the KAJAANI FS-100 Optical Fibre Length Analyzer which operates on a different principle. The FS-100 has a capillary tube and an optical system monitoring the passage of fibres over the active analyzer portion. The analyzer portion consists of a light source, polarized light filters, optical elements, and a light sensitive sensor. A suspension is sucked into the capillary tube by vacuum. The shape of the tube enables the fibers to be oriented in a longitudinal direction. Light emitted from the source disposed at one side of the capillary tube passes through the polarized light filter, capillary, another polarized light filter, and finally impinges on the light sensitive sensor. Due to a change in polarized light provoked by the presence of fiber in the capillary tube, a fiber image is formed on the light sensitive sensor by means of the optical elements. The light sensitive sensor has a plurality of sections and, depending on the number of sections activated, the number and length of fibers is determined by an electronic circuit. This arrangement is rather complex and expensive.

SUMMARY OF THE INVENTION

It is an object of this invention to eliminate said drawbacks and to provide an apparatus where the fibers would enter the place of measurement rectified as to their position in the direction of their carrying medium and at a speed substantially equal to the speed of the carrying medium.

The sensor according to this invention is of sandwich shape and a fiber rectifier with an inlet and outlet part is attached thereto. The sensor comprises an upper electrode, a central insulating part and a lower electrode, whereby the lower surface of the inlet part of the fiber rectifier is in close contact with the upper electrode, and the upper surface of the outlet part of the rectifier is in close contact with the lower electrode. Electric conductors are connected both to the upper and lower electrode of the sensor. The openings of the inlet part of the rectifier, of the sensor, and of the outlet part of the fiber rectifier are aligned and form together a channel for the suspension entering said channel in the direction of the arrow shown in the attached drawing.

An advantage of the apparatus according to this invention is that due to provision of the fiber rectifier, fibers are, at the place of measurement, oriented in the direction of flow of the carrying medium, have substantially the same speed as the carrying medium and the suspension can be sucked-off without a residuum being left. Another advantage is the relatively easy construction of the apparatus. The sandwich structure of the sensor can be formed for example by gluing or sintering a layer of polytetrafluorethylene (PTFE) applied on electrodes of the sensor.

The inlet part of the fiber rectifier can simultaneously form a storage vessel for the suspension. The outlet part thereof can also be a part of a vessel, into which the suspension is sucked-off due to underpressure.

By interconnection of the sensor with the inlet and outlet part of the fiber rectifier by means of a disassemblable armature, the whole apparatus can be easily disassembled for cleaning.

Advantages of the electric conductivity sensor for measuring the length and number of fibers in a suspension as compared to known optical devices for this purpose are its small dimensions and weight, its incomparably reduced complexity, simple assembling and adjustability of coaxiality of the sensor with the inlet and outlet part of the fiber rectifier.

BRIEF DESCRIPTION OF THE DRAWING

With these and other objects in view, which will become apparent in the following detailed description, the present invention, which is shown by example only, will be clearly understood in connection with the accompanying drawing, in which:

The single FIGURE shows an exemplary embodiment of the invention is indicated in a longitudinal sectioal view of an apparatus for measuring the length and number of fibers in an aqueous suspension.

DESCRIPTION OF THE PREFERRED EMBODIMENT

The apparatus as shown in the drawing comprises a sensor 1 and a fiber rectifier 2. The fiber rectifier 2 comprises an inlet part 3 and an outlet part 4. The sensor 1 comprises an upper electrode 5, a central insulating part 6 and a lower electrode 7. The lower surface of the inlet part 3 of the rectifier 2 is in close contact with the upper electrode 5 of the sensor 1, the upper surface of the outlet part 7 of the rectifier 2 being in close contact with the lower electrode 7 of the sensor 1. Electrical conductors 8, 9 are connected respectively both to the upper electrode 5 and to the lower electrode 7 of the sensor 1, whereby the opening of the inlet part 3 of the rectifier 2, the opening of the sensor 1 and the opening of the outlet part 4 of the rectifier 2 are aligned and their thus connected openings form a channel for the suspension entering said channel in the direction of the indicated arrow.

The device according to this invention operates so that a suspension of lower concentration contained in storage vessel is sucked on by way of the device into a collecting vessel. The electrodes of the sensor are by way of their conductors 8, 9 connected to an electrical evaluating apparatus where variations of the conductivity in the interelectrode space of the sensor 1 are registered. The evaluating apparatus registers changes of conductivity of the suspension in said interelectrode space and the duration of said changes to thereby calculate the number and length of fibers which have passed the through the sensor.

The sensor 1 of sandwich shape has the advantage that is can be easily connected to the inlet part 3 and to the outlet part 4 of the fiber rectifier 2. Both the inlet part 3 and the outlet part 4 of the fiber rectifier 2 are made of electrically non-conductive material. The electrodes 5 and 7 are made of corrosion resistant material. The central insulating part 6 is made of a material with high electric specific resistance capable of maintaining it in case of prolonged soaking in water. The thickness of the insulating part 6 of the sensor 1 is smaller or equal to the length of the shortest measured fiber.

The electrodes 5 and 7 are, by way of electric conductors 8, 9, connected to an electric circuit 10 for measuring variations of conductivity. When the channel of the pick-up means is only filled by distilled water, its electric conductivity has a certain magnitude. When the carrying medium in the distilled water contains some fibers, possibly also other particles are present, the conductivity of which is different from the conductivity of the carrying medium, a change of electric conductivity in the space between the electrodes 5 and 7 takes place during passage of the suspension through the opening of the sensor 1. When the speed of the suspension in the interelectrode space is stabilized, the evaluating arrangement connected to the electric conductors 8, 9 evaluates impulses, the time of duration of which is proportional to the length of the fibers and the number of impulses is equal to the number of fibers or particles which have passed through the opening of the sensor 1.

The opening of the inlet part 3 of the rectifier 2 has the tapered shape as indicated in the drawing. The speed of the carrying medium passing in the indicated direction increases due to the narrowing cross section of the opening of said inlet 3, so that the fibers contained in the suspension are oriented in the direction of the flow. In the zone around the electrode 5, the fiber is oriented in the direction of flow of the carrying medium of the suspension and the speed of the fiber is rather equal to the speed of the carrying medium. The cross section of the outlet part 4 is, in the zone close to the electrode 7, equal to the cross section of the opening of the sensor 1. A reduction of the speed of flow of the carrying medium in the outlet part 4 takes place only within a zone of larger cross section. The zone of constant speed of the carrying medium in openings of the inlet part 3 and the outlet part 4 of the rectifier 2 have a length larger or equal to the maximum length of a fiber. A stable speed of the suspension in the channel of the sensor 1 is secured by a constant underpressure in the collecting vessel for the suspension, connected to the outlet part 4 of the rectifier 2.

The device according to this invention can be applied for such suspensions of fibers or other particles, the conductivity of which is different from the conductivity of the carrying medium.

Although the invention is described and illustrated with reference to a single embodiment thereof, it is to be expressly understood that it is in no way limited to the disclosure of such preferred embodiment but is capable of numerous modifications within the scope of the appended claims.

I claim:

1. An apparatus for measuring the number and length of fibers in an aqueous solution comprising
   a fiber rectifier, said rectifier having a central throughbore, an inlet part and an outlet part;
   a pair of parallel arranged plate-like electrodes, said pair of electrodes being disposed in sequence between said inlet part and said outlet part of said rectifier;
   said electrodes being provided with a central opening arranged in alignment with the throughbore of said rectifier;
   measuring means connected to said electrodes for measuring conductivity and duration;
   whereby an aqueous solution flowing through said throughbore comes in contact with said electrodes and said measuring means measures the conductivity of said solution against time to determine the number and length of fibers in said solution.

2. An apparatus as claimed in claim 1 further comprising an insulating part disposed between said electrodes.

3. An apparatus as claimed in claim 1 wherein said throughbore is tapered from a larger diameter to a smaller in said inlet part.

4. An apparatus as claimed in claim 1 wherein said throughbore is tapered from a smaller diameter to a larger diameter in said outlet part.

5. An apparatus as claimed in claim 3 wherein said throughbore is tapered from a smaller diameter to a larger diameter in said outlet part.

6. An apparatus as in claim 3 wherein the solution flows past said electrodes at a constant speed.

7. An apparatus as in claim 4 wherein the solution flows past said electrodes at a constant speed.

* * * * *